United States Patent [19]

Weijand

[11] Patent Number: 5,792,212
[45] Date of Patent: Aug. 11, 1998

[54] NERVE EVOKED POTENTIAL MEASUREMENT SYSTEM USING CHAOTIC SEQUENCES FOR NOISE REJECTION

[75] Inventor: Koen J. Weijand, Hoensbroek, Netherlands

[73] Assignee: Medtronic, Inc., Minneapolis, Minn.

[21] Appl. No.: 812,292

[22] Filed: Mar. 7, 1997

[51] Int. Cl.$^6$ .................... A61N 1/32; A61B 5/05
[52] U.S. Cl. ............................... 607/73; 600/554
[58] Field of Search .................. 607/39–52, 62, 607/63, 72, 73, 117, 118; 128/741; 600/554

[56] References Cited

U.S. PATENT DOCUMENTS

| | | | |
|---|---|---|---|
| 4,431,000 | 2/1984 | Butler et al. | 607/73 |
| 4,571,556 | 2/1986 | Gnerlich et al. | 607/73 |
| 4,641,317 | 2/1987 | Fullerton | 375/1 |
| 4,743,906 | 5/1988 | Fullerton | 342/27 |
| 4,813,057 | 3/1989 | Fullerton | 375/37 |
| 4,867,164 | 9/1989 | Zabara | 607/72 X |
| 4,979,186 | 12/1990 | Fullerton | 375/23 |
| 5,143,081 | 9/1992 | Young et al. | 128/741 |
| 5,522,386 | 6/1996 | Lerner | 128/630 |
| 5,571,150 | 11/1996 | Wernicke et al. | 607/72 |

FOREIGN PATENT DOCUMENTS

| | | | |
|---|---|---|---|
| 2122904 | 1/1984 | United Kingdom | 607/73 |
| 2162066 | 1/1986 | United Kingdom | 607/73 |

OTHER PUBLICATIONS

Rijkhoff, Nico J.M., et al., "Selective Stimulation of Sacral Nerve Roots for Bladder Control: a Study by Computer Modeling," IEEE Transactions on Biomedical Engineering, vol. 41, No. 5, May 1994, pp. 413–423.

Sweeney, James D., et al., "A Nerve Cuff Technique for Selective Excitation of Peripheral Nerve Trunk Regions," IEEE Transactions on Biomedical Engineering, vol. 37, No. 7, Jul. 1990, pp. 706–715.

*Primary Examiner*—Jeffrey R. Jastrzab
*Attorney, Agent, or Firm*—Michael J. Jaro; Harold Patton

[57] ABSTRACT

There is provided a measurement system for measuring signals evoked in response to stimulus pulses applied to a nerve, muscle or like physiological portion of a patient. The measurement system is characterized by delivering stimulus pulses at randomly generated intervals, and enabling the sense circuitry to track the timing of the stimulus pulse generation so as to aid in discriminating the evoked response pattern from surrounding noise. Specifically, after each stimulus pulse a delay is timed out for a time corresponding to the expected latency between the delivered pulse and the arrival of the evoked response at another location. The delay signal is then used to initiate time out of a window which controls operation of the sensing circuit for a window duration corresponding to when the evoked response pattern is appearing. Limiting the sensing operation to the window duration enables tracking of the response pattern, and minimizes power consumption. The sensed evoked response signals are further processed to provide control signals for adjustment of the delay and window, thereby optimizing the sensing operation. The measurement system is suitably part of a larger implantable stimulus system, which includes the ability to adjust pulse-to-pulse interval, or rate, and also pulse output level as a function of measured evoked response patterns. In a further embodiment, the stimulus system involves steering of stimulus pulses to selected nerve fibers or muscle tissue, and the measurement system provides feedback for adjusting the steering parameters.

24 Claims, 3 Drawing Sheets

NERVE EVOKED POTENTIAL MEASUREMENT SYSTEM USING CHAOTIC SEQUENCES FOR NOISE REJECTION

FIELD OF THE INVENTION

This invention lies in the area of nerve stimulation systems and, more particularly, systems having a capability of measuring evoked potentials in order to determine efficacy of the stimulus parameters.

BACKGROUND OF THE INVENTION

The detection of low level physiological signals, and particularly neural signals, has long presented significant difficulty and has been a subject of continuous research. For nerve stimulation systems, it is desirable to be able to measure evoked potentials in order to determine the efficacy of the stimulating system and to determine what, if any, parameter adjustments are desirable. This is important at the initial time of introducing the system, and remains important due to changes in conditions. For example, even the slightest re-positioning of the stimulus electrodes can have a significant effect on the stimulus response pattern, and thus the therapeutic effect. Stimulus efficacy can change for varying reasons, such as electrode charge build up, chemical deterioration of the nerve system, regrowth of nerve fibers, etc. Consequently, it is important to maintain a reliable system for monitoring stimulus efficacy. The problem in measuring such evoked potentials is that the signals involved are very weak and are difficult to pick out of attendant noise. This places special requirements on the instrumentation system in terms of electrodes, amplifier circuits, and filters.

Various techniques and methods have been proposed for evaluating stimulus systems, and specifically evoked response patterns. See, for example, U.S. Pat. No. 5,143,081, which describes a dual pulse arrangement for obtaining data from which to judge variations in stimulus responses as a function of stimulus frequency and amplitude. However, such systems provide only a protocol for obtaining useful types of data under measurement conditions where it is assumed that the signals can be sensed, and do not address the fundamental problem of discriminating the very small evoked potential signals from the noise so as to get useful signals in the first instance.

This invention is based in part on known information transmission theory, the principles of which are adapted in a novel arrangement for sensing evoked potentials. As stated by Shannon, "A Mathematical Theory of Communication," *Bell Syst. Techn. J.*, Vol.27 (1948), channel capacity (C) is related to transmission bandwidth (W), signal power (S) and noise power (N) as follows:

$$C = W \log_2 (1+S/N).$$

This shows that channel capacity can be increased in the face of a low S/N ratio by increasing effective bandwidth. This fact has been exploited in various communication systems, including spread spectrum, or time domain communication systems. However, the principle of providing an expanded bandwidth has not been utilized in the area of real time sensing of physiologic signals, and there has been no effective solution for applying this principle in this important area. Particularly for implanted or other types of battery powered stimulus systems, any solution must be low power, i.e., the measurement must involve a minimal amount of processing and energy consumption.

Accordingly, it is an object of this invention to provide a measurement system particularly suitable for low power consumption medical devices, and which provides for improved noise rejection and low current drain signal detection circuitry. The system improves noise rejection by randomizing the timing of delivering stimulus pulses, thereby using an effectively high bandwidth to transmit the stimulus information along a channel, e.g., a nerve fiber trunk; and a correlation process such as a synchronized sense window or demodulator, to recapture the received low bandwidth information.

SUMMARY OF THE INVENTION

There is provided a measurement system for measuring evoked response signals in a physiological stimulus system, providing for improved detection of low level evoked response signals. In a preferred embodiment of a nerve stimulus system, a stimulus generator is provided which is controlled to deliver stimulus pulses with a chaotic sequence of random pulse-to-pulse intervals, and sense circuitry, e.g., signal detection circuitry, is provided with timing that is synchronized to the stimulus pulses so that the evoked response pattern can be picked out from the noise. The timing is achieved by delaying the stimulus signal by a delay that corresponds to the nerve complex latency period, or the time between delivery of the stimulus to a first location and occurrence of evoked response at a second location. The delayed signal initiates a window circuit which enables the sense circuitry for a predetermined window duration which is timed to encompass the evoked response pattern. Further processing circuitry analyzes each evoked response pattern and provides for adjustment of the delay and/or window interval, thereby maximizing resultant signal to noise ratio and minimizing the operative duty cycle of the sense amplifier, thereby reducing power consumption.

In a preferred embodiment, the measurement system is a part of an implantable stimulus device. The measurement results are utilized to adjust the stimulus pattern so as to provide more effective therapy. For example, the output level of delivered stimulus pulses can be adjusted as a function of the measured evoked response patterns. In yet a further embodiment, the stimulus system includes adjustment of the electrode configuration being used, to provide selective excitation. In another embodiment, pulse parameters of the stimulus pulses are varied in order to steer the resulting electric fields, thereby providing another mechanism for selecting the nerves or muscle portions that are stimulated. In these systems, measurement data is utilized for controlling the selection and/or steering operations.

DESCRIPTION OF THE PREFERRED EMBODIMENTS

Figure 1A:
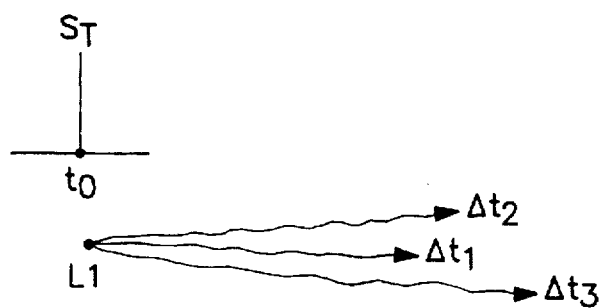
FIG. 1A is a representation of a stimulus pulse $S_T$ which is delivered to a trunk of nerve fibers at a location L1, with an indication of the respective times for the evoked potential to be propagated across respective different nerves to a second location where it is sensed.
Figure 1B:
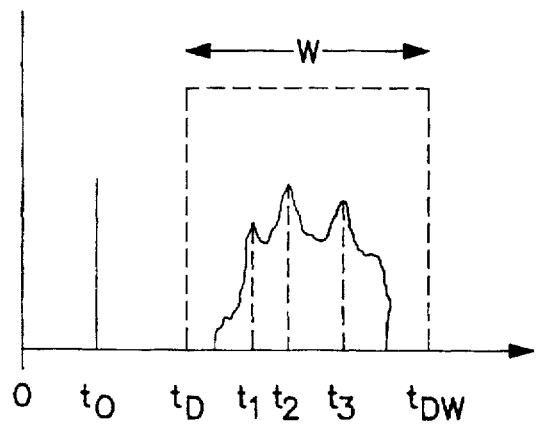
FIG. 1B is a timing diagram indicating the timing of the evoked response pattern relative to the delivery of a stimulus pulse, and indicating a window of duration W which is initiated after delay $\Delta t_D$ following delivery of the stimulus pulse.

Referring now to FIGS. 1A and 1B, there are shown representations of the delivery of a stimulus pulse $S_T$ at time $t_0$ to a trunk of nerve fibers, and the subsequent detection of an evoked response pattern at a downstream location on the trunk of nerve fibers. Since different nerve fibers can have respective different latencies, or periods until an evoked response appears, the pattern of sensed evoked response signals, as seen in FIG. 1B, reflects the different latency durations. Thus, a nerve 1 may have an evoked response which appears $\Delta t_1$, after delivery of the stimulus pulse, such that a corresponding relative peak is shown at time $t_1 = t_0 + \Delta t_1$. Likewise, nerve 2 yields an evoked response $\Delta t_2$ after delivery of the stimulus pulse, resulting in a sensed peak at $t_2 = t_0 + \Delta t_2$; and nerve 3 produces a sensed peak at $t_3 = t_0 + \Delta t_3$. It is an object of the measurement system to be able to sense these different evoked response portions of the signal, to determine arrival times and thus the response of respective faster and slower nerves to stimulus pulses of different amplitudes. As indicated in FIG. 1B, the timing window W, initiated after a delay $\Delta t_D$, commences at a time $t_D$ and ends at time $t_{DW}$, and is positioned to enable the sensing amplifier and associated circuitry to sense signals only during the window duration W, thereby blocking out other extraneous signals. Of course, in any particular application, it may be desirable to expand or reduce the duration W, or the delay $\Delta t_D$, to enable exploration for different responses to different stimulus pulse parameters.

Figure 2:
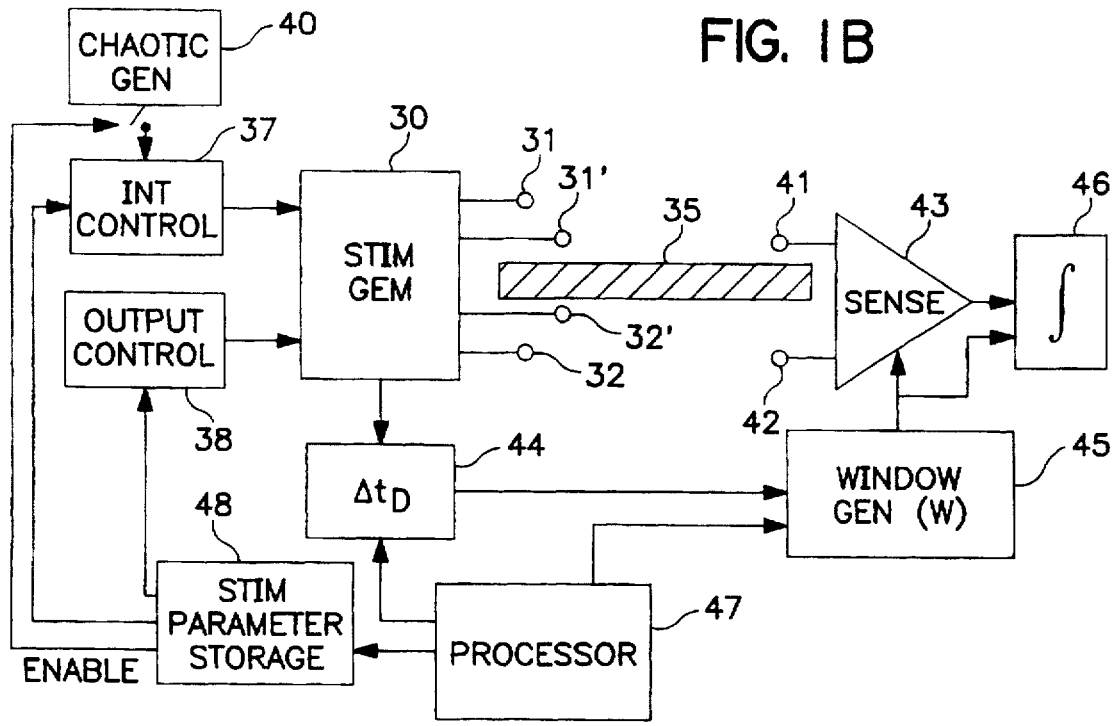
FIG. 2 is a block diagram of a stimulus and measurement system in accordance with this invention.

Referring now to FIG. 2, there is shown a stimulus generator 30, which provides output stimulus pulses across electrodes 31, 32. Electrodes 31, 32 are positioned to stimulate a trunk 35 of nerve fibers, according to a determined protocol, for effecting therapy. Additional electrodes, 31', 32' are shown, for use in providing selective stimulation and/or steering stimulation, as discussed in greater detail below. The parameters of the pulses delivered by stimulus generator 30 are controlled by interval control circuit 37, which controls the spacing or time interval between successive pulses; and output control 38, which controls the amplitude and/or width of the stimulus pulses. Thus, blocks 30, 37 and 38 combined represent a controllable stimulus generator.

For the evoked potential measurement of this invention, a pair of sensing electrodes 41, 42 is positioned at a predetermined distance from electrodes 31, 32, for sensing potential signals evoked by stimulus pulses. After the evoked potentials have propagated along nerve trunk 35, the signals sensed at electrodes 41, 42 are amplified and processed by circuit 43. The operation of circuit 43 is synchronized with the delivery of stimulus pulses by circuits 44 and 45. Circuit 44 receives a signal corresponding to the initiation of a stimulus at $t_0$, and generates an output following a variable delay $\Delta t_D$. The output is connected to window generator circuit 45, which generates a window signal as illustrated in FIG. 1B, which is connected to enable amplifier circuit 43. The window signal is also connected to integrator 46, which provides an output which is the integral of the received and processed signals, and is representative of the total power in the sensed evoked potential pattern. By using the window signal to turn on circuits 43 and 46 only during the time that the signal is expected, a considerable savings of energy is achieved.

In the preferred embodiment of this invention, during a measurement of evoked potentials, chaotic generator 40 is connected to interval control 37, and provides a randomly generated interval signal such that the interval between successive stimulus pulses from generator 30 is varied randomly. As indicated, sense circuit 43 continues to track the evoked responses due to the feed forward circuit of delay 44 and window 45. Thus, while the interval between successive stimulus signals varies, the window tracks this variance and thus synchronizes the sensing operation to the random timing of the delivered stimulus pulses.

The output of integrator 46 is connected to processor 47, which can provide any one of a variety of processing operations; additionally, the output from sense circuit 43 can also be connected directly to circuit 47, to provide, e.g., timing data such as $t_1$, $t_2$ and $t_3$ shown in FIG. 1B. Thus, the output can be averaged, it can be analyzed to integrate the power of received signals and compare with past values, etc. This processing is suitably done with the aid of a microprocessor and stored software, but can also be carried out by hardware, either in analog form or digital form incorporating DSP techniques. An output of processor 47 is suitably connected to delay block 44 and window generator 45, to adjust the timing and duration of the window, thereby to optimize the measurement response the patient situation. Thus, whatever the patient posture, electrode positioning, etc., the stimulus conditions are reflected in the processed signal and used to control the window operation. An output from the processor is also connected to stimulus parameter storage block 48, for use during non-measurement, or ongoing stimulus conditions. Thus, an output is connected to amplitude or pulse width control block 38, and another output is connected to interval control block 37, so that ongoing stimulus parameters are optimally adjusted. Processor 47 also may contain timing means for enabling connection of the chaotic generator 40, and also for enabling operation of the entire measurement system, i.e., circuits 43–46.

Figure 3:
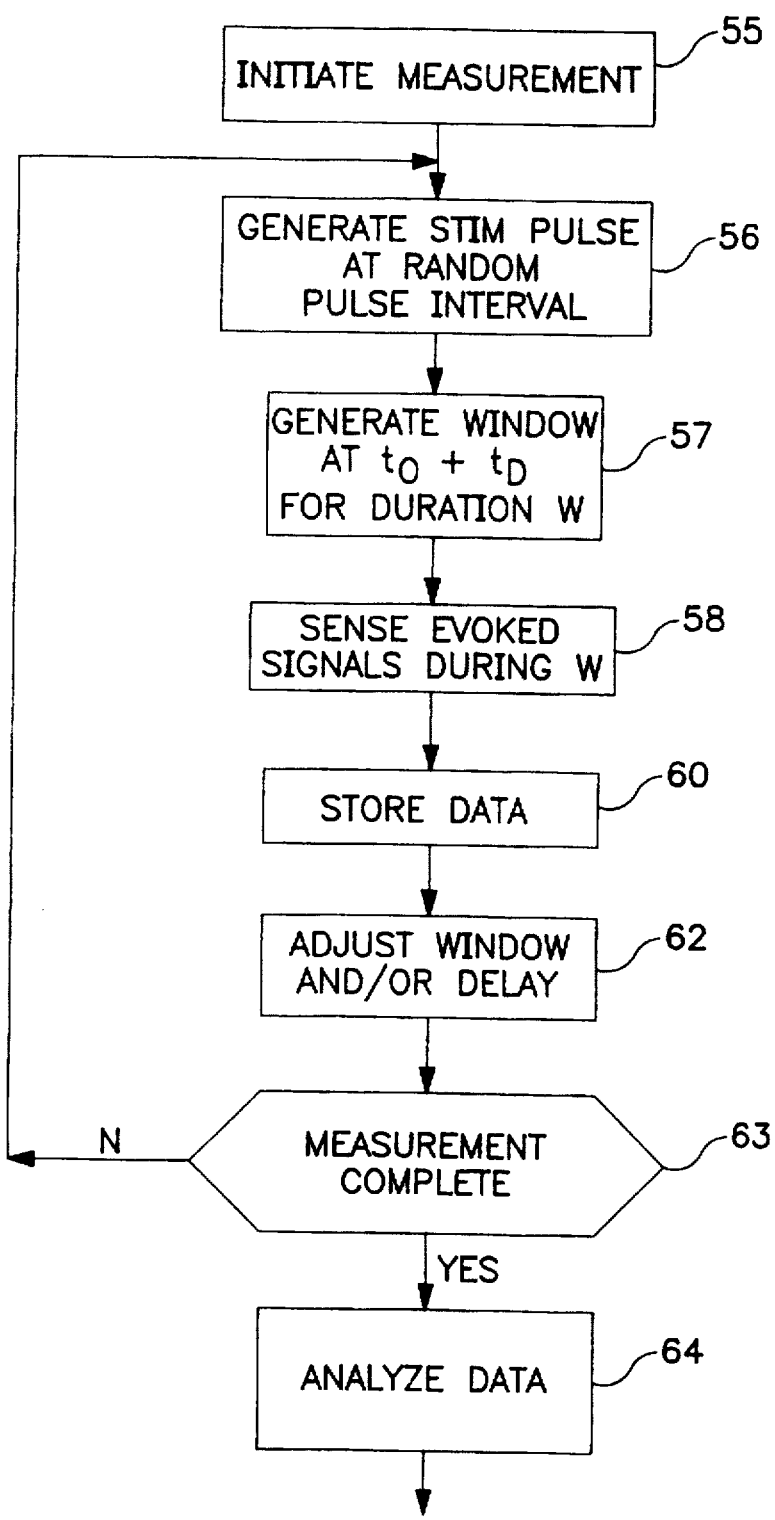
FIG. 3 is a flow diagram of the primary steps in a method of measuring evoked potentials in accordance with this invention.

Referring now to FIG. 3, there is shown a flow diagram illustrating the primary steps in carrying out the measuring method of this invention. As indicated at 55, the measurement is initiated. This may be done directly by a physician, or for an implanted system it may be done, for example, upon command from an external programmer in communication with processor block 47. At 56, a stimulus pulse is generated and delivered to the body location, e.g., a nerve fiber trunk. As discussed above, the pulse intervals are randomized. At 57, a window of duration W is generated starting at a delay $\Delta t_D$ following the stimulus pulse. At 58, the evoked signals are sensed at the electrodes and processed during the signal W, and the signal data is stored at 60. Thus, step 58 includes the integration function illustrated at 46 in FIG. 46; arrival times and power peak data are stored during step 60. At 62, the window and/or delay are adjusted, if the data suggest this. At 63, it is determined whether the measurement is complete. For instance, 100 or more events may be required to obtain sufficient data to determine how to make significant adjustments. Until the data meets the criteria established for a complete test, the method loops back to 56, for delivery of the next stimulus pulse at a random interval. When the measurement is complete, the data is analyzed at 64, and the measurement is over. Of course, the analyzed data may suggest further measurement, in which case the measurement is re-initiated. As set forth in FIG. 4, the analyzed data are used to adjust the stimulus parameters for subsequent stimulation of the patient.

As indicated above in relation to FIG. 2, additional stimulus electrodes may be utilized for selection of the nerve fibers to be stimulated. Thus, while two additional electrodes 32', 32' are illustrated, it is to be understood that any number of stimulus electrodes may be provided, so that different electrode configurations can be utilized depending upon the measurement results. Further, the electrodes may have different geometries for providing additional selectivity. Further, plural electrode configurations may be utilized for steering stimulus pulses, in a known manner. See, for example, U.S. Pat. No. 5,501,703, incorporated herein by reference, which discloses a multi-channel pulse generator driving a plurality of electrodes, to each of which is delivered stimulus pulses with parameters adapted to steer the electrical stimulation field. In the system of this invention, generator 30 may provide plural pulses. The measured response pattern, both in terms of the measured power and arrival times, is utilized to control the electrode configuration, as well as the pulse output parameters.

Figure 4:
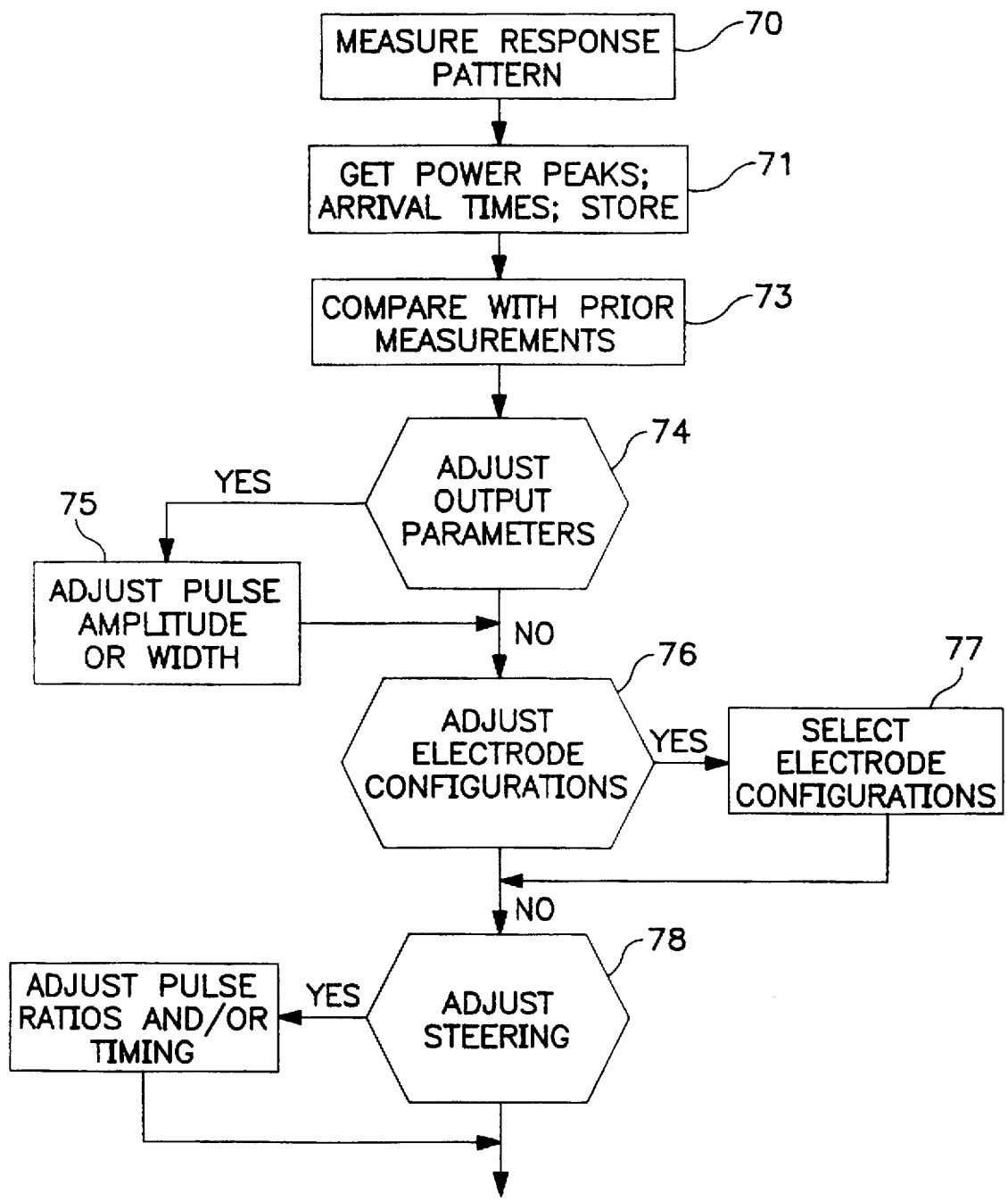
FIG. 4 is a flow diagram of the primary steps of an illustrative procedure for adjusting stimulus conditions based on measurements, in accordance with this invention.

Referring to FIG. 4, there is shown a flow diagram which sets forth the primary steps taken in a closed loop system in accordance with this invention. As indicated at block 70, the response pattern to delivered stimulus pulses is measured, in accordance with the steps set forth in FIG. 3. Following this, at step 71, the power peaks and arrival times of the response pattern are obtained, and stored. Next, at 73 the device optionally compares the new measurements with prior stored measurements. At 74, the measured data and the comparison data are processed, and it is determined whether pulse output parameters are to be adjusted. If yes, at 75, the pulse amplitude or width of one or more stimulus pulses is adjusted. At 76, it is determined whether the electrode configurations are to be adjusted. If yes, at 77 an alternate electrode configuration is selected. At 78, it is determined whether steering is to be adjusted, in the event that steering is being utilized. If yes, pulse amplitude ratios and relative timing are adjusted, based on the measurement data.

It is to be noted that the apparatus of this invention may be used with different test protocols. Thus, it may be desired to vary amplitude control in accordance with a predetermined program, during a measurement routine, in order to get information concerning stimulus threshold or efficiency of capturing different nerve fibers. Such a measurement protocol may be introduced by processor 47, or may be introduced through an external programmer indicated at 50, which is used to program memory within processor 47.

It is seen that the system of this invention achieves the dual objectives of improving signal detection, i.e., sensing of evoked potentials, and minimizing power consumption. By randomizing delivery of the pulses, the effective bandwidth of transmission is increased; by providing correlated or synchronized reception, the data is demodulated, resulting in improved noise rejection. Further, by turning on the amplifier only when a signal is expected, power consumption is minimized.

While the invention has been described primarily in terms of stimulating nerves, it is broadly applicable to different therapies. For example, it can be used for selective stimulation of scrawl nerve roots, for control of incontinence; for epidural spinal cord stimulation; for brain stimulation; etc. Likewise, it can be used for stimulation of selected organs or muscles.

What is claimed is:

1. An evoked potential measurement system in an implantable nerve stimulator apparatus, comprising:

stimulus generator means for generating and delivering stimulus pulses to a first location on a trunk of nerve fibers, having chaotic sequence means for controlling said generator means to generate said stimulus pulses in a chaotic sequence with random intervals, electrode means for sensing evoked signals in said nerve fibers at a second location on said trunk, and circuit means for processing said sensed evoked signals, sync means for synchronizing the timing of the operation of said circuit means with the timing of generating said stimulus pulses, and measure means operative after each said stimulus pulse for obtaining from said processed signals a measure of the sensed evoked signals corresponding to said each stimulus pulse.

2. The system as described in claim 1, wherein said sync means comprises delay means connected to said generator means for providing a delay signal at a delay following each generated stimulus pulse, and enable means for enabling said circuit means to operate for a predetermined duration after said delay signal is generated.

3. The system as described in claim 1, further comprising a window circuit for generating a time window following each said delay signal, and wherein said sense means comprises circuit means for processing sensed evoked signals and said enable means has means for turning on said circuit means only during each said window.

4. The system as described in claim 3, wherein said measure means comprises integrator means for integrating said sensed evoked signals following each said stimulus pulse to obtain said measure.

5. The system as described in claim 4, comprising processing means for processing a plurality of said measures and for obtaining a delay adjustment signal as a function of said processing, and adjusting means for adjusting said delay with said delay adjustment signal.

6. The system as described in claim 3, further comprising data means for storing data representative of sensed evoked signals, adjust means for obtaining an output adjustment signal as a function of said data, and control means for controlling said stimulus generator means in a non-measurement mode, said control means having output control means for controlling the amplitude or width of said stimulus pulses with said output adjustment signal.

7. The system as described in claim 6, comprising means for determining from said data an effective time duration for said window, and window control means for controlling the time duration of said window to correspond to said effective time duration.

8. An implantable system for stimulating patient nerve fibers, comprising:

controllable stimulus means for generating and delivering nerve stimulus pulses of controllable rate and output level to a first patient nerve location, said generator normally operating at a controllable rate and output level;

evoked potential measurement means operative during a test period for obtaining measures of evoked potentials produced by said delivered pulses at a sense location, having chaotic sequence means for controlling said generator to generate said stimulus pulses at substantially random intervals, sense means for sensing and processing potentials evoked by said delivered stimulus pulses at a said sense location, said sense means having circuitry for processing said potentials, window means for controlling said circuitry to process said evoked signals only during a window of time following each said stimulus pulse, said window means having delay means for delaying the start of said window by a delay with respect to each said stimulus pulse, measure means for obtaining a measure of the evoked potentials sensed by said sensing means during each said window; and adjust means for adjusting one or more parameters of said stimulus pulses as a function of said measures.

9. The system as described in claim 8, comprising measurement adjust means for adjusting said delay and said window as a function of said measures.

10. The system as described in claim 8, comprising means for initiating a test period.

11. The system as described in claim 8, wherein said controllable stimulus means comprises a plurality of electrodes, and configuration means for selecting a configuration of said electrodes as a function of said measures.

12. The system as described in claim 11, wherein said measure means comprises arrival means for determining arrival times of evoked responses.

13. The system as described in claim 8, wherein said controllable stimulus means comprises means for delivering plural pulses, each of said pulses being characterized by a set of output pulse parameters, and wherein said adjust means comprises means for adjusting each respective set of output pulse parameters so as to control steering of the stimulus electrical field.

14. The system as described in claim 8, wherein said adjust means comprises output means for adjusting one or both of the rate and output level of said stimulus pulses as a function of said measures.

15. The system as described in claim 14, wherein said output means comprises means for adjusting both amplitude and pulse width of said stimulus pulses.

16. A system for measuring the responses of a patient body portion to applied stimulus pulses, comprising:

controllable pulse generator means for generating and delivering stimulus pulses to a first location of said body portion, having random control means for controlling generation of said stimulus pulses at random pulse-to-pulse intervals, delay means for generating a delay signal at a delay following each said stimulus pulse, window means for generating a timing window initiated by each said delay signal, and sense means for sensing, at a second location of said body portion, signals evoked by said stimulus pulses, circuit means for processing said sensed signals, and on-off means for turning said circuit means on only during each said timing window, whereby said processing is time synchronized to said random pulse-to-pulse intervals.

17. The system as described in claim 16, wherein said patient body portion is a group of nerve fibers, and said pulse generator means comprises first electrode means for delivering said stimulus pulses to said first location, and said said sense means comprises second electrode means for sensing evoked signals at said second location.

18. A method of measuring evoked responses to stimulus pulses applied to nerves of a patient, comprising:

generating stimulus pulses with random pulse-to-pulse intervals, and delivering said pulses to a first patient nerve location, generating a window enable signal in timed relation to the delivery of each said stimulus pulse, sensing signals evoked by said stimulus pulses at a second nerve patient location, and processing said sensed signals only during each said window enable signal.

19. The method as described in claim 18, comprising timing out a delay following each said delivered pulse, and initiating said window enable signal upon time out of each said delay.

20. The method as described in claim 19, comprising obtaining and storing data representative of said evoked responses following a plurality of delivered stimulus pulses, and determining when sufficient data has been obtained to complete a measurement.

21. The method as described in claim 20, comprising adjusting said delay as a function of said data.

22. The method as described in claim 20, comprising adjusting the duration of said window enable signal as a function of said data.

23. The method as described in claim 20, comprising analyzing said data after a completed measurement, adjusting one or more parameters of said stimulus pulses and said window, and performing another measurement using said adjusted parameters.

24. A system for automatically controlling stimulation of nerve fibers, comprising:

stimulating means for stimulating nerve fibers, determining means for determining characteristics of evoked responses in said nerve fibers due to said stimulating, selecting means for selecting excitation of certain nerve fibers as a function of said determined characteristics, and controlling means for controlling said stimulus means so as to selectively excite said selected certain nerve fibers.

* * * * *